(12) United States Patent
Parham et al.

(10) Patent No.: US 11,581,495 B2
(45) Date of Patent: *Feb. 14, 2023

(54) PHENYL DERIVATIVES SUBSTITUTED WITH AT LEAST TWO ELECTRON ACCEPTORS AND AT LEAST TWO ELECTRON DONORS FOR USE IN ORGANIC ELECTRONIC DEVICES

(71) Applicant: Merck Patent GmbH, Darmstadt (DE)

(72) Inventors: Amir Hossain Parham, Frankfurt Am Main (DE); Philipp Stoessel, Frankfurt Am Main (DE); Christof Pflumm, Darmstadt (DE); Anja Jatsch, Frankfurt Am Main (DE); Joachim Kaiser, Darmstadt (DE)

(73) Assignee: MERCK PATENT GMBH, Darmstadt (DE)

( * ) Notice: Subject to any disclaimer, the term of this patent is extended or adjusted under 35 U.S.C. 154(b) by 296 days.

This patent is subject to a terminal disclaimer.

(21) Appl. No.: 15/746,228

(22) PCT Filed: Jul. 1, 2016

(86) PCT No.: PCT/EP2016/001119
§ 371 (c)(1),
(2) Date: Jan. 19, 2018

(87) PCT Pub. No.: WO2017/012694
PCT Pub. Date: Jan. 26, 2017

(65) Prior Publication Data
US 2018/0226586 A1 Aug. 9, 2018

(30) Foreign Application Priority Data
Jul. 23, 2015 (GB) .................................. 1513037

(51) Int. Cl.
*H01L 51/50* (2006.01)
*H01L 51/00* (2006.01)
(Continued)

(52) U.S. Cl.
CPC ........ *H01L 51/0072* (2013.01); *C07D 209/80* (2013.01); *C07D 209/86* (2013.01); *C07D 209/88* (2013.01); *C07D 219/02* (2013.01); *C07D 219/04* (2013.01); *C07D 241/48* (2013.01); *C07D 265/38* (2013.01); *C07D 279/20* (2013.01); *C07D 471/04* (2013.01); *C07F 5/027* (2013.01); *C07F 7/0816* (2013.01); *C08G 61/124* (2013.01); *C08G 73/0672* (2013.01); *H01L 51/008* (2013.01); *H01L 51/0035* (2013.01); *H01L 51/0036* (2013.01); *H01L 51/0039* (2013.01); *H01L 51/0043* (2013.01); *H01L 51/0071* (2013.01); *H01L 51/0094* (2013.01); *C08G 2261/11* (2013.01); *C08G 2261/12* (2013.01); *C08G 2261/132* (2013.01); *C08G 2261/226* (2013.01); *C08G 2261/228* (2013.01); *C08G 2261/3142* (2013.01); *C08G 2261/3241* (2013.01); *C08G 2261/3245* (2013.01); *C08G 2261/3246* (2013.01); *C08G 2261/3247* (2013.01); *C08G 2261/364* (2013.01); *C08G 2261/41* (2013.01); *C08G 2261/411* (2013.01);
(Continued)

(58) Field of Classification Search
None
See application file for complete search history.

(56) References Cited

U.S. PATENT DOCUMENTS

2004/0170863 A1* 9/2004 Kim ........................ C07C 13/72
428/690
2007/0007882 A1* 1/2007 Fukuoka ............. H01L 51/0051
313/503
(Continued)

FOREIGN PATENT DOCUMENTS

EP 2039737 A2 3/2009
EP 2851408 A1 3/2015
(Continued)

OTHER PUBLICATIONS

Zhang et al., Highly efficient and color-stable hybrid warm white organic light-emitting diodes using a blue material with thermally activated delayed fluorescence; 2014, Journal of Materials Chemistry C: Materials for Optical and Electronic Devices, 2(38), 8191-8197 (Year: 2014).*
Cho, Y., et al., "20% External Quantum Efficiency in Solution-Processed Blue Thermally Activated Delayed Fluorescent Devices", Advanced Functional Materials, vol. 25, No. 43, (2015), pp. 6786-6792.
FILE CAplus, Chemical Abstracts: Columbus, OH; Accession No. 1270, Taiyuan University of Technology, Peoples Republic of China, "Thermal activation type delayed fluorescent material based on 4-fluorophenylacetonitrile and its preparation and application", Peoples Republic of China Patent 105602553A, May 25, 2016, XP-002761410.
(Continued)

*Primary Examiner* — Gregory D Clark
(74) *Attorney, Agent, or Firm* — Faegre Drinker Biddle & Reath LLP

(57) ABSTRACT

The present invention relates to a phenyl-derivative compound substituted with at least two electron acceptors and at least two electron donors. Formula (I) $R^A{}_a R^D{}_b R^S{}_c C_6$ wherein a is 2, 3 or 4; b is 2, 3 or 4; c is 0, 1 or 2; a+b−c=6; $R^A$ is at each occurrence independently a group with −M-effect; $R^B$ is at each occurrence independently a group with +−M-effect; $R^S$ is as defined in claim 1. Said compound is suited for use in organic electronic devices, particularly in organic electroluminescent devices.

12 Claims, No Drawings

(51) Int. Cl.

| | | |
|---|---|---|
| *C07D 209/86* | (2006.01) | |
| *C07D 209/88* | (2006.01) | |
| *C07D 209/80* | (2006.01) | |
| *C07D 219/02* | (2006.01) | |
| *C07D 219/04* | (2006.01) | |
| *C07D 241/48* | (2006.01) | |
| *C07D 265/38* | (2006.01) | |
| *C07D 279/20* | (2006.01) | |
| *C07D 471/04* | (2006.01) | |
| *C07F 5/02* | (2006.01) | |
| *C07F 7/08* | (2006.01) | |
| *C08G 61/12* | (2006.01) | |
| *C08G 73/06* | (2006.01) | |

(52) U.S. Cl.
CPC . *C08G 2261/412* (2013.01); *C08G 2261/414* (2013.01); *C08G 2261/514* (2013.01); *C08G 2261/95* (2013.01); *H01L 51/0002* (2013.01); *H01L 51/5012* (2013.01); *H01L 51/5072* (2013.01); *H01L 51/5088* (2013.01); *H01L 51/5096* (2013.01)

(56) References Cited

U.S. PATENT DOCUMENTS

| | | | |
|---|---|---|---|
| 2014/0131686 A1* | 5/2014 | Kawakami | C07D 495/22 257/40 |
| 2015/0105564 A1* | 4/2015 | Adachi | C07D 209/18 548/440 |
| 2015/0129849 A1* | 5/2015 | Kwong | H01L 51/0059 257/40 |
| 2015/0228904 A1 | 8/2015 | Kawamura et al. | |
| 2016/0072076 A1 | 3/2016 | Stoessel et al. | |
| 2016/0211466 A1 | 7/2016 | Ogiwara et al. | |
| 2017/0256720 A1* | 9/2017 | Adachi | C09K 11/06 |
| 2017/0369773 A1 | 12/2017 | Parham et al. | |

FOREIGN PATENT DOCUMENTS

| | | |
|---|---|---|
| EP | 3015457 A1 | 5/2016 |
| WO | WO-2014146752 A1 | 9/2014 |
| WO | WO-2015070944 A1 | 5/2015 |
| WO | WO-2015175678 A1 | 11/2015 |
| WO | WO-2015195837 A1 | 12/2015 |
| WO | WO-2016091353 A1 | 6/2016 |

OTHER PUBLICATIONS

FILE CAplus, Chemical Abstracts: Columbus, OH; Accession No. 1274, Kunshan Guoxian Photoelectric Co., Ltd.; Tsinghua University, "Preparation of red-light heat-activated delayed fluorescent material and organic electroluminescent device", Peoples Republic of China Patent 105418533A, Mar. 23, 2016, XP-002761409.

FILE CAplus, Chemical Abstracts: Columbus, OH; Accession No. 1287, Shu at al., "Simulated evolution of fluorophores for light emitting diodes", Journal of Chemical Physics, vol. 142, No. 10, (2015), p. 104104/1-104104-11, XP-002761408.

FILE CAplus, Chemical Abstracts: Columbus, OH; Accession No. 1299, Konica Minolta Holdings Inc., "Organic photoelectric conversion components having dicyclohexylpyrrole derivative carrier transport layers", World Intellectual Property Organization Patent 2011093309A1, Jun. 6, 2013, XP-002761407.

FILE CAplus, Chemical Abstracts: Columbus, OH; Accession No. 1298, SFC Co., Ltd., "Pyridine derivative compounds as electroluminescent material for organic electroluminescent element", Republic of Korea Patent 20120072787A, Jul. 4, 2012, XP-002761406.

International Search Report for PCT/EP2016/001119 dated Sep. 23, 2016.

Kim, M., et al., "Highly efficient and color tunable thermally activated delayed fluorescent emitters using a "twin emitter" molecular design", Chemical Communications, vol. 52, No. 2, (2015), pp. 339-342.

Rosokha, S., et al., "Very Fast Electron Migrations within p-Doped Aromatic Cofacial Arrays Leading to Three-Dimensional (Toroidal) π-Delocalization", Journal of the American Chemical Society, vol. 128, No. 29, (2006), pp. 9394-9407.

Uoyama, H., et al., "Highly efficient organic light-emitting diodes from delayed fluorescence", Nature, vol. 492, (2012), pp. 234-238.

Written Opinion of the International Searching Authority for PCT/EP2016/001119 dated Sep. 23, 2016.

* cited by examiner

PHENYL DERIVATIVES SUBSTITUTED WITH AT LEAST TWO ELECTRON ACCEPTORS AND AT LEAST TWO ELECTRON DONORS FOR USE IN ORGANIC ELECTRONIC DEVICES

CROSS-REFERENCE TO RELATED APPLICATIONS

This application is a national stage application (under 35 U.S.C. § 371) of PCT/EP2016/001119, filed Jul. 1, 2016, which claims benefit of Great British Application No. 1513037.0, filed Jul. 23, 2015, both of which are incorporated herein by reference in their entirety.

TECHNICAL FIELD

The present invention relates to a phenyl-derivative compound substituted with at least two electron acceptors and at least two electron donors. Said compound is suited for use in organic electronic devices, particularly in organic electroluminescent devices.

BACKGROUND

Organic electronic devices, i.e. electronic devices comprising a layer which is mostly made of an organic material, offer a number of advantages over conventional electronic devices based on inorganic materials. Organic electronic devices allow for example good processability in combination with improved final properties such as flexibility and/or reduced weight. Frequently, such devices are also characterized by extremely low energy consumption. Properties like these are of considerable interest for example for handheld devices, such as tablet-PCs and smart phones.

A particular example of organic electronic devices are organic electroluminescent devices (OLEDs). The term "organic electroluminescent device" is generally used for an electronic device which comprises at least one organic material that emits light when an electric current is applied. OLEDs in general as well as their structure are for example disclosed in U.S. Pat. No. 4,539,507, U.S. Pat. No. 5,151,629, EP 0676461 and WO 98/27136.

Though progress has been made there remains considerable interest in improving the properties of organic electronic devices, particularly of organic electroluminescent devices, such as for example in terms of life time, efficiency and operating voltage. Important factors in this respect are organic light emitting layers, and particularly the materials comprised therein, as well as organic charge transporting layers.

It is therefore an object of the present invention to find novel materials having improved properties. Additionally, it is an object of the present invention to further increase the pool of available materials suited for use in organic electronic devices in general and organic electroluminescent devices in particular. Furthermore, it is a particular object of the present invention to increase the pool of materials emitting light of blue color. Further objects of the present invention will become evident from the following description as well as from the examples.

SUMMARY

The present inventors have now surprisingly found that the above objects may be attained either individually or in any combination by the present compound as well as by further aspects of the present application.

The present application therefore provides for a compound of general formula (I)

$$R^A_a R^D_b R^S_c C_6 \quad (I)$$

wherein a is 2, 3 or 4; b is 2, 3 or 4; c is 0, 1 or 2; a+b+c=6;

$R^A$ is at each occurrence independently a group with $-M$-effect;

$R^D$ is at each occurrence independently a group with $+-M$-effect;

$R^S$ is at each occurrence independently selected from the group consisting of is at each occurrence independently selected from the group consisting of H, D, F, Cl, Br, I, $B(OR^2)_2$, CHO, $C(=O)R^2$, $CR^2=C(R^2)_2$, CN, $C(=O)OR^2$, $C(=O)N(R^2)_2$, $Si(R^2)_3$, $N(R^2)_2$, $NO_2$, $P(=O)(R^2)_2$, $OSO_2R^2$, $OR^2$, $S(=O)R^2$, $S(=O)_2R^2$, OH, SH, linear alkyl-, alkoxy- or thioalkyl-group with 1 to 20 C-atoms or a branched or cyclic alkyl-, alkoxy- or thioalkyl-group with 3 to 20 C-atoms or a alkenyl- or alkinyl-group with 2 to 20 C-atoms, wherein these groups may be substituted with one or more of groups $R^2$ and wherein one or more $CH_2$— Gruppen in these groups may be replaced by $-R^2C=CR^2-$, $-C\equiv C-$, $Si(R^2)_2$, $C=O$, $C=S$, $C=NR^2$, $-C(=O)O-$, $-C(=O)NR^2-$, $NR^2$, $P(=O)(R^2)$, $-O-$, $-S-$, SO or $SO_2$, and wherein one or more H-atoms in these groups may be replaced by D, F, Cl, Br, I, CN or $NO_2$, or an aromatic or heteroaromatic ring system with 5 to 60 aromatic ring atoms, which can be substituted with one or more groups $R^2$, or an aryloxy- or heteroaryloxy-group with 5 to 60 aromatic ring atoms, which can be substituted with one or more groups $R^2$, or an aralkyl- or heteroaralkyl-group with 5 to 60 aromatic ring atoms, which can be substituted with one or more groups $R^2$, wherein two or more groups $R^2$ may be linked with each other and form an aliphatic or aromatic or heteroaromatic ring;

$R^2$ is at each occurrence independently selected from group consisting of H, D, F, aliphatic, aromatic and/or heteroaromatic hydrocarbyl group with 1 to 20 C-atoms, in which one or more hydrogen atoms may be replaced by F, wherein two or more groups $R^2$ together may form a mono- or polycyclic aliphatic ring system.

provided that for (i) a=2, b=4 and c=0; or (ii) a=b=c=2 and the two groups $R^S$ being in para-position to each other, and the two groups $R^A$ being in ortho-position to each other and the two groups $R^D$ being in ortho-position to each other, $R^A$ is not —CN and $R^D$ is not carbazol or a substituted carbazol.

The present application also provides for a formulation comprising a solvent and said compound.

Further, the present application provides for a method for producing an electronic device, said process comprising the steps of (a) providing said compound or an oligomer, polymer or dendrimer comprising such compound; and (b) depositing said compound or said oligomer, polymer or dendrimer on a supporting layer In addition, the present application provides for organic electronic devices, particularly for organic electroluminescent devices, comprising said compound.

DETAILED DESCRIPTION

Definitions

For the purposes of the present application the terms "organic light emitting, device" and "organic electroluminescent device" are used interchangeably.

For the purposes of the present application the terms "group" and "substituent" are used synonymously.

For the purposes of the present application the term "substituted" is meant to denote a substituent $R^2$ as defined in the present application.

In the formulae of the present application a double bond may be used to denote an aromatic bond in an aromatic or heteroaromatic ring system.

The mesomeric effect, in the present application denoted as "M-effect", is attributed to a substituent or group due to overlap of its p- or π-orbitals with the p- or π-orbitals of the rest of the molecular entity. Delocalization is thereby introduced or extended, and electronic charge may flow to or from the substituent. See International Union of Pure and Applied Chemistry, Compendium of Chemical Technology, Gold Book, Version 2.3.2, 2012-08-19. Groups with a +M-effect ("positive M-effect") donate electron density to the mesomeric system. Groups with a −M-effect ("negative M-effect") accept electron density from the mesomeric system.

In the present application $R^1$ is at each occurrence independently selected from the group consisting of H, D, F, Cl, Br, I, $B(OR^2)_2$, CHO, $C(=O)R^2$, $CR^2=C(R^2)_2$, CN, $C(=O)OR^2$, $C(=O)N(R^2)_2$, $Si(R^2)_3$, $N(R^2)_2$, $NO_2$, $P(=O)(R^2)_2$, $OSO_2R^2$, $OR^2$, $S(=O)R^2$, $S(=O)_2R^2$, OH, SH, linear alkyl-, alkoxy- or thioalkyl-group with 1 to 20 C-atoms or a branched or cyclic alkyl-, alkoxy- or thioalkyl-group with 3 to 20 C-atoms or a alkenyl- or alkinyl-group with 2 to 20 C-atoms, wherein these groups may be substituted with one or more of groups $R^2$ and wherein one or more $CH_2$-groups in these groups may be replaced by $-R^2C=CR^2-$, $-C\equiv C-$, $Si(R^2)_2$, $C=O$, $C=S$, $C=NR^2$, $-C(=O)O-$, $-C(=O)NR^2-$, $NR^2$, $P(=O)(R^2)$, $-O-$, $-S-$, SO or $SO_2$, and wherein one or more H-atoms in these groups may be replaced by D, F, Cl, Br, I, CN or $NO_2$, or an aromatic or heteroaromatic ring system with 5 to 60 aromatic ring atoms, which can be substituted with one or more groups $R^2$, or an aryloxy- or heteroaryloxy-group with 5 to 60 aromatic ring atoms, which can be substituted with one or more groups $R^2$, or an aralkyl- or heteroaralkyl-group with 5 to 60 aromatic ring atoms, which can be substituted with one or more groups $R^2$, wherein two or more groups $R^2$ may be linked with each other and form an aliphatic or aromatic or heteroaromatic ring.

In the present application $R^2$ is at each occurrence independently selected from the group consisting of H, D, F, alkyl having from 1 to 20 C-atoms, aromatic groups having from 1 to 20 aromatic carbon atoms and heteroaromatic groups having from 1 to 20 aromatic ring atoms, wherein the aromatic groups and the heteroaromatic groups may be substituted with an alkyl having from 1 to 20 carbon atoms. For $R^2$ preferred exemplary alkyls having from 1 to 20 C-atoms may be selected from the group consisting of methyl, ethyl, n-propyl, i-propyl, n-butyl, i-butyl, s-butyl, t-butyl, 2-methylbutyl, n-pentyl, s-pentyl, cyclopentyl, neopentyl, n-hexyl, cyclohexyl, neo-hexyl, n-heptyl, cycloheptyl, n-octyl, cyclooctyl, and 2-ethylhexyl. For $R^2$ preferred exemplary aromatic groups having from 1 to 20 aromatic carbon atoms and heteroaromatic groups having from 1 to 20 aromatic ring atoms may be selected from the group consisting of benzene, naphthaline, anthracene, benzanthracene, phenanthrene, benzphenanthrene, pyrene, chrysene, perylene, fluoranthene, naphthacene, pentacene, benzpyrene, biphenyl, biphenylene, terphenyl, terphenylene, quaterphenyl, fluorene, spirobifluorene, dihydrophenanthrene, dihydropyrene, tetrahydropyrene, cis- or trans-indenofluorene, truxene, isotruxene, spirotruxene, spiroisotruxene, furane, benzofurane, isobenzofurane, dibenzofurane, thiophene, benzothiophene, isobenzothiophene, dibenzothiophene, pyrrole, indole, isoindole, carbazole, indolocarbazole, indenocarbazole, pyridine, chinoline, isochinoline, acridine, phenanthridine, benzo-5,6-chinoline, benzo-6,7-chinoline, benzo-7,8-chinoline, phenothiazine, phenoxazine, pyrazole, indazole, imidazole, benzimidazole, naphthimidazole, phenanthrimidazole, pyridimidazole, pyrazinimidazole, chinoxalinimidazole, oxazole, benzoxazole, naphthoxazole, anthroxazole, phenanthroxazole, isoxazole, 1,2-thiazole, 1,3-thiazole, benzothiazole, pyridazine, benzopyridazine, pyrimidine, benzpyrimidine, chinoxaline, 1,5-diazaanthracene, 2,7-diazapyrene, 2,3-diazapyrene, 1,6-diazapyrene, 1,8-diazapyrene, 4,5-diazapyrene, 4,5,9,10-tetraazaperylene, pyrazine, phenazine, phenoxazine, phenothiazine, fluorubin, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine, benzothiadiazole as well as their alkyl substituted derivatives, with the alkyl having from 1 to 20 C-atoms.

In the present application $R^3$ is at each occurrence independently selected from the group consisting of F, linear alkyl- or alkoxy-group with 1 to 20 C-atoms, a branched or cyclic alkyl- or alkoxy-group with 3 to 20 C-atoms, each of which may be substituted with one or more of groups $R^2$, wherein one or more non-adjacent $CH_2$-groups may be replaced by $R^2C=CR^2$, $C\equiv C$, $Si(R^2)_2$, $C=O$, $NR^2$, O, S or $CONR^2$, and wherein one or more H-atom may be replaced with D or F, or an aromatic or heteroaromatic ring system with 5 to 24 aromatic ring atoms, each of which may each be substituted with one or more of groups $R^2$, or an aryloxy- or heteroaryloxy-group with 5 to 24 aromatic ring atoms, which can be substituted with one or more groups $R^2$, or an aralkyl- or heteroaralkyl-group with 5 to 24 aromatic ring atoms, which can be substituted with one or more groups $R^2$, wherein two $R^2$ bound to the same carbon atom may from an aliphatic or aromatic ring system and thus a spiro system; or $R^3$ can form together with a neighboring group $R^1$ or $R^2$ an aliphatic ring system.

For the purposes of the present invention linear, branched or cyclic alkyl-, alkenyl- and alkinyl-groups may preferably be selected from the group consisting of methyl, ethyl, n-propyl, i-propyl, n-butyl, i-butyl, s-butyl, t-butyl, 2-methylbutyl, n-pentyl, s-pentyl, cyclopentyl, neo-pentyl, n-hexyl, cyclohexyl, neo-hexyl, n-heptyl, cycloheptyl, n-octyl, cyclooctyl, 2-ethylhexyl, trifluoromethyl, pentafluoroethyl, 2,2,2-trifluorethyl, ethenyl, propenyl, butenyl, pentenyl, cyclopentenyl, hexenyl, cyclohexenyl, heptenyl, cycloheptenyl, octenyl, cyclooctenyl, ethinyl, propinyl, butinyl, pentinyl, hexinyl, octinyl, and the respective substituted derivatives, wherein they may be substituted with one or more of groups $R^2$ and wherein one or more $CH_2$-groups in these groups may be replaced by $-R^2C=CR^2-$, $-C\equiv C-$, $Si(R^2)_2$, $C=O$, $C=S$, $C=NR^2$, $-C(=O)O-$, $-C(=O)NR^2-$, $NR^2$, $P(=O)(R^2)$, $-O-$, $-S-$, SO or SO$_2$, and wherein one or more H-atoms in these groups may be replaced by D, F, Cl, Br, I, CN or NO$_2$.

For the purposes of the present invention, linear or branched alkoxy- and thio- alkyl-, alkenyl- and alkinyl-groups may preferably be selected from the group consisting of methoxy, trifluoromethoxy, ethoxy, n-propoxy, i-propoxy, n-butoxy, i-butoxy, s-butoxy, t-butoxy, n-pentoxy, s-pentoxy, 2-methylbutoxy, n-hexoxy, cyclohexyloxy, n-heptoxy, cycloheptyloxy, n-octyloxy, cyclooctyloxy, 2-ethylhexyloxy, pentafluoroethoxy, 2,2,2-trifluorethoxy, methylthio, ethylthio, n-propylthio, i-propylthio, n-butylthio, i-butylthio, s-butylthio, t-butylthio, n-pentylthio, s-pentylthio, n-hexylthio, cyclohexylthio, n-heptylthio, cycloheptylthio, n-octylthio, cyclooctylthio, 2-ethyl hexylthio, trifluoromethylthio, pentafluoroethylthio, 2,2,2-trifluorethylthio, ethenylthio, propenylthio, butenylthio, pentenylthio, cyclopentenylthio, hexenylthio, cyclohexenylthio, heptenylthio, cycloheptenylthio, octenylthio, cyclooctenylthio, ethinylthio, propinylthio, butinylthio, pentinylthio, hexinylthio, heptinylthio, octinylthio, and the respective substituted derivatives, wherein they may be substituted with one or more of groups R$^2$ and wherein one or more CH$_2$-groups in these groups may be replaced by —R$^2$C=CR$^2$—, —C≡C—, Si(R$^2$)$_2$, C=O, C=S, C=NR$^2$, —C(=O)O—, —C(=O)NR$^2$—, NR$^2$, P(=O)(R$^2$), —O—, —S—, SO or SO$_2$, and wherein one or more H-atoms in these groups may be replaced by D, F, Cl, Br, I, CN or NO$_2$.

For the purposes of the present invention an aromatic ring system preferably has from 6 to 60 aromatic ring atoms, most preferably from 6 to 30 aromatic ring atoms. For the purposes of the present invention a heteroaromatic ring system preferably has from 5 to 60 aromatic ring atoms, most preferably from 5 to 30 aromatic ring atoms, at least one of which is a heteroatom. Suitable heteroatoms may be selected from the group consisting of N, O and S. The terms "aromatic ring system" and "heteroaromatic ring system" as used herein may also denote a system in which several aryl- or heteroaryl-groups are connected by non-aromatic units. Preferably such non-aromatic units comprise at most 10% of the atoms comprised in the aromatic or heteroaromatic ring system, which are different from H and D. Examples of suitable non-aromatic units may be selected from the group consisting of sp$^3$-hybridized atoms with the atom selected from the group consisting of C, Si, N and O, sp$^2$-hybridized C-atom, sp$^2$-hybridized N-atom, and sp-hybridized C-atom. For the purposes of the present application systems such as for example 9,9'-spirobifluorene, 9,9'-diarylfluorene, tri-arylamine, diarylether, stilbene as well as systems, in which two or more aryl groups are connected for example by means of a linear or cyclic alkyl-, alkenyl- or alkinyl-group of a silyl-group, are to be considered as aromatic rings systems. Furthermore for the purposes of the present application systems, in which one or more aryl- or heteroaryl-groups are connected by means of one or more single bonds, such as for example biphenyl, terphenyl or diphenyltriazine, are to be considered as aromatic or heteroaromatic systems.

Examples of suitable aromatic or heteroaromatic ring systems, which may optionally be substituted as defined above and optionally be linked at any position on the aromatic or heteroaromatic ring as defined in the present application, are preferably selected from the group consisting of benzene, naphthaline, anthracene, benzanthracene, phenanthrene, benzphenanthrene, pyrene, chrysene, perylene, fluoranthene, naphthacene, pentacene, benzpyrene, biphenyl, biphenylene, terphenyl, terphenylene, quaterphenyl, fluorene, spirobifluorene, dihydrophenanthrene, dihydropyrene, tetrahydropyrene, cis- or trans-indenofluorene, truxene, isotruxene, spirotruxene, spiroisotruxene, furane, benzofurane, isobenzofurane, dibenzofurane, thiophene, benzothiophene, isobenzothiophene, dibenzothiophene, pyrrole, indole, isoindole, carbazole, indolocarbazole, indenocarbazole, pyridine, chinoline, isochinoline, acridine, phenanthridine, benzo-5,6-chinoline, benzo-6,7-chinoline, benzo-7,8-chinoline, phenothiazine, phenoxazine, pyrazole, indazole, imidazole, benzimidazole, naphthimidazole, phenanthrimidazole, pyridimidazole, pyrazinimidazole, chinoxalinimidazole, oxazole, benzoxazole, naphthoxazole, anthroxazole, phenanthroxazole, isoxazole, 1,2-thiazole, 1,3-thiazole, benzothiazole, pyridazine, benzopyridazine, pyrimidine, benzpyrimidine, chinoxaline, 1,5-diazaanthracene, 2,7-diazapyrene, 2,3-diazapyrene, 1,6-diazapyrene, 1,8-diazapyrene, 4,5-diazapyrene, 4,5,9,10-tetraazaperylene, pyrazine, phenazine, phenoxazine, phenothiazine, fluorubin, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine, benzothiadiazole and any combination as well as derivatives thereof.

Examples of aryl and heteroaryl groups, said groups optionally being substituted as defined above and optionally being linked at any position on the aromatic or heteroaromatic ring as defined in the present application, are preferably selected from the group consisting of benzene, naphthaline, anthracene, phenanthrene, pyrene, dihydropyrene, chrysene, perylene, fluoranthene, benzanthracene, benzphenanthrene, tetracene, pentacene, benzpyrene, furane, benzofurane, isobenzofurane, dibenzofurane, thiophene, benzothiophene, isobenzothiophene, dibenzothiophene, pyrrole, indole, isoindole, carbazole, pyridine, chinoline, isochinoline, acridine, phenanthridine, benzo-5,6-chinoline, benzo-6,7-chinoline, benzo-7,8-chinoline, phenothiazine, phenoxazine, pyrazole, indazole, imidazole, benzimidazole, naphthimidazole, phenanthrimidazole, pyridimidazole, pyrazinimidazole, chinoxalinimidazole, oxazole, benzoxazole, naphthoxazole, anthroxazole, phenanthroxazole, isoxazole, 1,2-thiazole, 1,3-thiazole, benzothiazole, pyridazine, benzopyridazine, pyrimidine, benzpyrimidine, chinoxaline, pyrazine, phenazine, naphthyridine, azacarbazole, benzocarboline, phenanthroline, 1,2,3-triazole, 1,2,4-triazol, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole.

For the purposes of the present application the terms "aryloxy-group" and "heteroaryloxy-group" are used to denote aryl- and heteroaryl-groups, respectively, as defined above, which are covalently bound via a divalent (ether-type) O-atom.

For the purposes of the present application, the terms "aralkyl-group" and "heteroaralkyl-group" are used to denote aryl- and heteroaryl-groups, respectively, wherein the aryl- or heteroaryl-group is substituted with an alkyl-group having from 1 to 20 C-atoms, wherein in the alkyl-group any H- or D-atom or any CH$_2$-group may be substituted with the above mentioned groups, and wherein the alkyl-group is used to bond the aryl- or heteroaryl-group to the remainder of the compound.

Compound

Generally stated, the present compounds are characterized by a phenyl-derived structure, which is substituted with at least two electron donor groups and at least two electron acceptor groups as defined herein.

Similar compounds have recently been disclosed by H. Uoyama et al., Nature, Vol. 492, 13 Dec. 2012, pages 234-238.

The present compounds can be represented by general formula (I)

$$R^A_a R^D_b R^S_c C_6 \qquad (I)$$

with $R^A$, $R^D$, $R^S$, a, b and c as defined herein.

Parameter a is 2, 3 or 4. Parameter b is 2, 3 or 4. Parameter c is 0, 1 or 2. Parameters a, b and c are selected independently of each other, provided that a+b+c=6.

Groups $R^A$ are independently of each other selected from groups having a −M-effect. Such groups are generally well known to the skilled person and can be found in many common textbooks on organic chemistry.

Preferred examples of groups $R^A$ may be selected from the group consisting of fluoroalkyl, F, $BR^1_2$, $B(OR^1)_2$, CHO, $C(=O)R^1$, CN, $C(=O)OR^1$, $C(=O)N(R^1)_2$, $CR^1=C(CN)_2$, $N_3$, $NO_2$, $P(=O)(R^1)_2$, $S(=O)R^1$, $S(=O)_2R^1$, heteroaryl, heteroaryl substituted with one or more electron withdrawing groups and aryl substituted with one or more electron withdrawing groups, wherein the electron withdrawing groups are selected from the group consisting of fluoroalkyl, F, $B(OR^1)_2$, CHO, $C(=O)R^1$, CN, $C(=O)OR^1$, $C(=O)N(R^1)_2$, $NO_2$, $P(=O)(R^1)_2$, $S(=O)R^1$, and $S(=O)_2R^1$, with $R^1$ as defined above.

More preferably, at each occurrence $R^A$ is independently selected from the group consisting of fluoroalkyl, F, $C(=O)R^1$, CN, heteroaryl, heteroaryl substituted with one or more electron withdrawing groups and aryl substituted with one or more electron withdrawing groups, wherein the electron withdrawing groups are selected from the group consisting of fluoroalkyl, F, $C(=O)R^1$, and CN, with $R^1$ as defined above.

Even more preferably at each occurrence $R^A$ is independently selected from the group consisting of fluoroalkyl, F, CN, heteroaryl, heteroaryl substituted with one or more electron withdrawing groups and aryl substituted with one or more electron withdrawing groups, wherein the electron withdrawing groups are selected from the group consisting of fluoroalkyl, F, CN.

Still even more preferably at each occurrence $R^A$ is independently selected from the group consisting of F and CN.

Most preferably $R^A$ is CN.

Groups $R^D$ are independently of each other selected from groups having a +M-effect. Such groups are generally well known to the skilled person and can be found in many common textbooks on organic chemistry.

Preferred examples of groups $R^D$ may be of general formula (II)

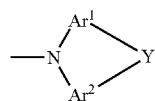

(II)

with $Ar^1$, $Ar^2$ and Y as defined herein.

$Ar^1$ and $Ar^2$ are independently of each other selected from unsubstituted aromatic ring systems with 6 to 60 aromatic ring atoms, substituted aromatic ring systems with 6 to 60 aromatic ring atoms, unsubstituted heteroaromatic ring systems with 5 to 60 aromatic ring atoms and substituted heteroaromatic ring systems with 6 to 60 aromatic ring atoms.

Suitable linking groups Y may for example be selected from the group consisting of a single bond, $BR^1$, $C(R^1)_2$, $Si(R^1)_2$, $NR^1$, $PR^1$, $P(=O)R^1$, $P(=S)R^1$, O, S, S=O and $S(=O)_2$, with $R^1$ as defined above.

Preferably said linking group Y may be selected from the group consisting of a single bond, $BR^1$, $C(R^1)_2$, $Si(R^1)_2$, $NR^1$, $P(=O)R^1$, O, S, and $S(=O)_2$, with $R^1$ as defined above.

More preferably said linking group Y may be selected from the group consisting of a single bond, $BR^1$, $C(R^1)_2$, $NR^1$, $P(=O)R^1$, O, and $S(=O)_2$, with $R^1$ as defined above.

Even more preferably said linking group Y may be selected from the group consisting of a single bond, $C(R^1)_2$, $NR^1$, and O, or alternatively from the group consisting of a single bond, $NR^1$, and O, with $R^1$ as defined above.

Still even more preferably said linking group Y may be selected from the group consisting of a single bond, and O.

Most preferably said linking group Y is a single bond.

Particularly suited are groups of formula (II) selected from the groups consisting of carbazoles, azacarbazoles, annealed carbazoles, annealed azacarbazoles, 5,10-dihydrophenazaboranes, 9,10-dihydroacridines, 9,10-dihydro-10-sila-acridines, 9,10-dihydro-phenazine, 10-hydro-phenoxazine, and 10-hydro-phentiazine, all of which may be substituted or unsubstituted.

Suitable examples of carbazoles and azacarbazoles and respective annealed derivatives are illustrated by the following formulae (N-1) to (N-11):

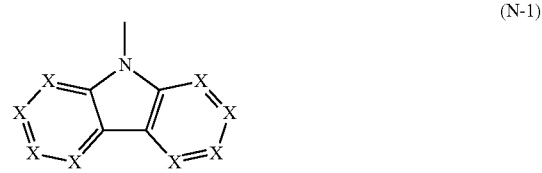

(N-1)

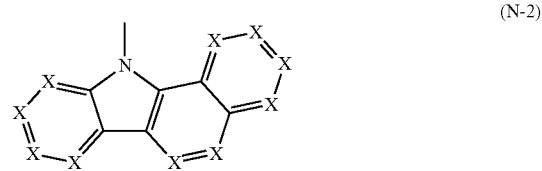

(N-2)

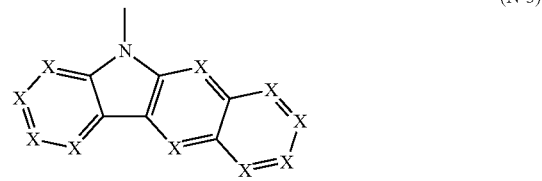

(N-3)

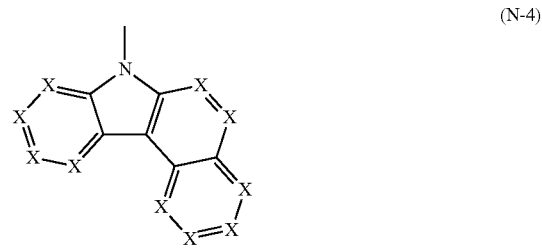

(N-4)

-continued

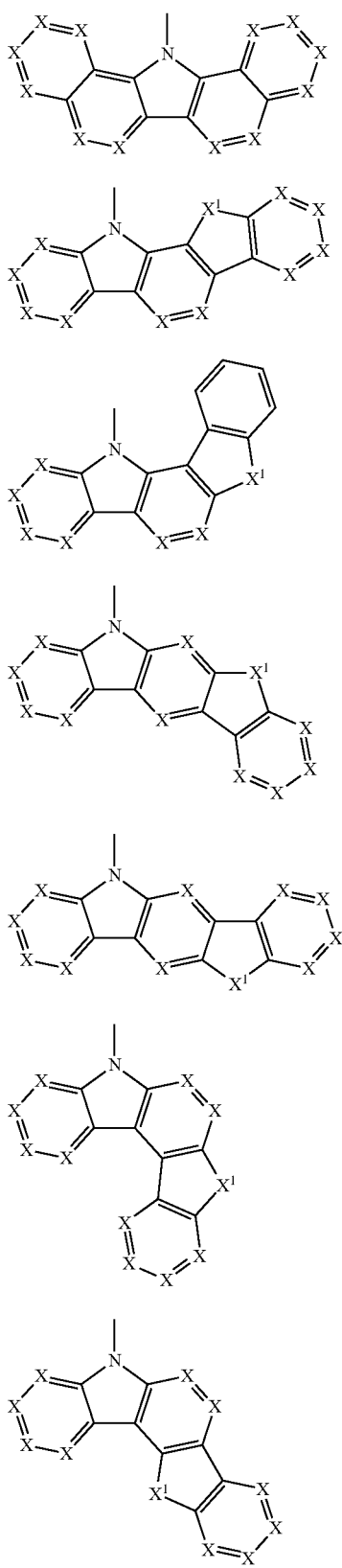

(N-5)

(N-6)

(N-7)

(N-8)

(N-9)

(N-10)

(N-11)

Suitable examples of 5,10-dihydro-phenazaboranes, 9,10-dihydroacridines, 9,10-dihydro-10-sila-acridines, 9,10-dihydro-phenazine, 10-hydro-phenoxazine, and 10-hydro-phentiazine are illustrated by the following formulae (N-12) to (N-16):

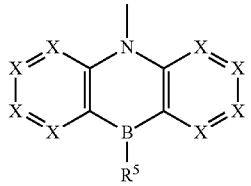

(N-12)

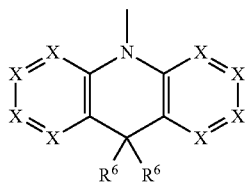

(N-13)

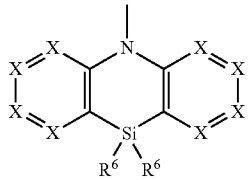

(N-13)

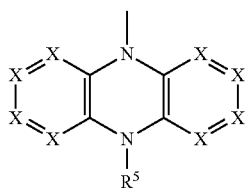

(N-15)

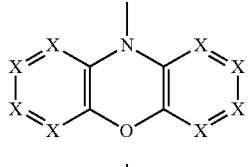

(N-15)

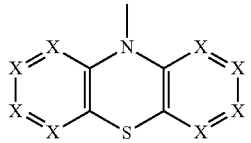

(N-16)

In above formulae (N-1) to (N-16)

X is N or $CR^4$ with $R^4$ being as defined above for $R^2$;

$X^1$ is $BR^2$, $CR^1_2$, $NR^2$, O or S; preferably $CR^1_2$, $NR^2$, O or S; most preferably $CR^1_2$ or $NR^2$, with $R^2$ as defined above;

$R^5$ is unsubstituted aryl, unsubstituted hetaryl, substituted aryl or substituted hetaryl, which—if substituted—are preferably substituted in the 2- and 6-positions with alkyl, aryl or CN; and $R^6$ is alkyl, unsubstituted aryl, unsubstituted hetaryl, substituted aryl or substituted hetaryl, which optionally may be linked by a group Y as defined above.

Groups $R^S$ are—if present—independently of each other selected from the group consisting as defined above for $R^1$. Preferred suitable examples for $R^S$ may be selected from the group consisting of H, alkyl having from 1 to 10 carbon atoms and alkyl having from 1 to 10 carbon atoms wherein one or more hydrogen atom is replaced by fluorine.

Suitable examples of compounds of formula (I) may be selected from the following formulae (I-A-1) and (I-A-2)

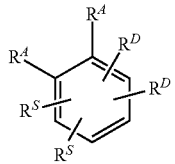
(I-A-1)

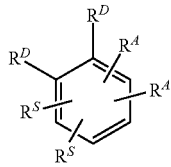
(I-A-2)

wherein a, b, c, $R^A$, $R^D$ and $R^S$ are as defined herein.

The present compounds of formula (I) may have the following composition with regards to parameters a, b and c:

|       | a | b | c |
|-------|---|---|---|
| (K-1) | 4 | 2 | 0 |
| (K-2) | 3 | 3 | 0 |
| (K-3) | 3 | 2 | 1 |
| (K-4) | 2 | 4 | 0 |
| (K-5) | 2 | 3 | 1 |
| (K-6) | 2 | 2 | 2 |

Examples with a=4, b=2 and c=0 may be selected from the list consisting of the following formulae (I-B-1) to (I-B-3):

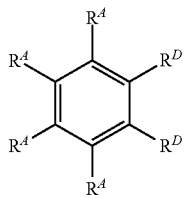
(I-B-1)

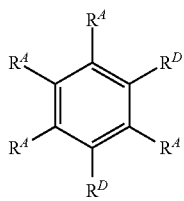
(I-B-2)

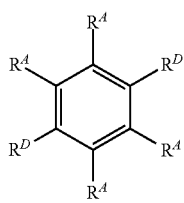
(I-B-3)

Examples with a=3, b=3 and c=0 may be selected from the list consisting of the following formulae (I-B-4) to (I-B-6):

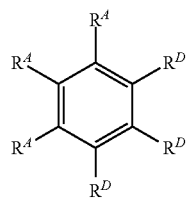
(I-B-4)

(I-B-5)

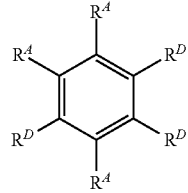
(I-B-6)

Examples with a=3, b=2 and c=1 may be selected from the list consisting of the following formulae (I-B-7) to (I-B-12):

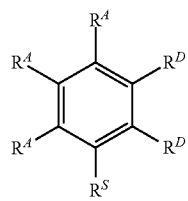
(I-B-7)

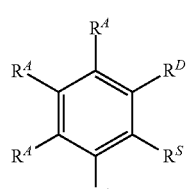
(I-B-8)

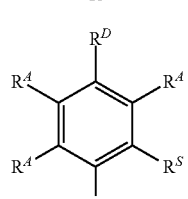
(I-B-9)

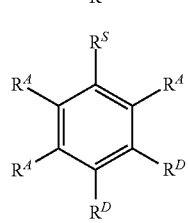
(I-B-10)

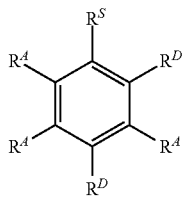 (I-B-11)
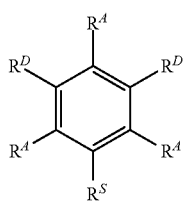 (I-B-12)
Examples with a=2, b=4 and c=0 may be selected from the list consisting of the following formulae (I-B-13) to (I-B-15):
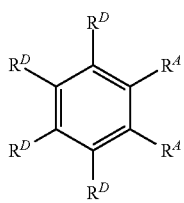 (I-B-13)
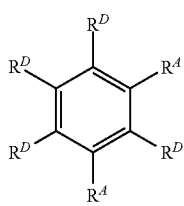 (I-B-14)
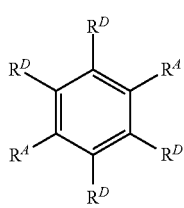 (I-B-15)
Examples with a=2, b=3 and c=1 may be selected from the list consisting of the following formulae (I-B-16) to (I-B-21):
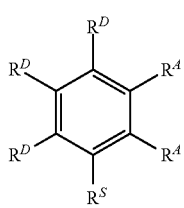 (I-B-16)
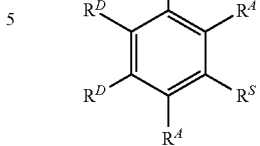 (I-B-17)
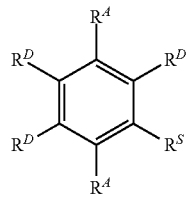 (I-B-18)
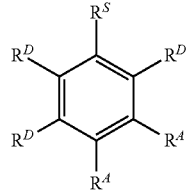 (I-B-19)
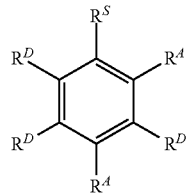 (I-B-20)
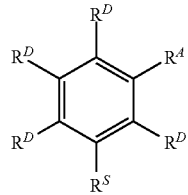 (I-B-21)
Examples with a=2, b=2 and c=2 may be selected from the list consisting of the following formulae (I-B-22) to (I-B-32):
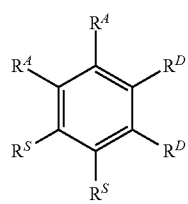 (I-B-22)
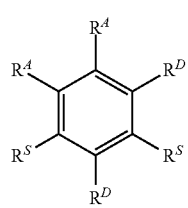 (I-B-23)

(I-B-24) 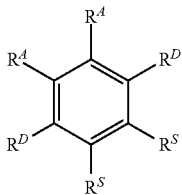

(I-B-25) 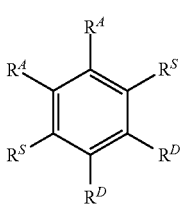

(I-B-26) 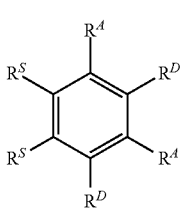

(I-B-27) 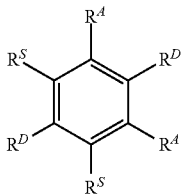

(I-B-28) 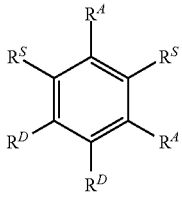

(I-B-29) 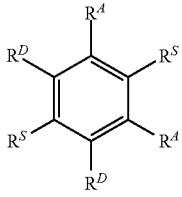

(I-B-30) 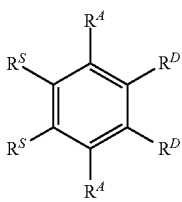

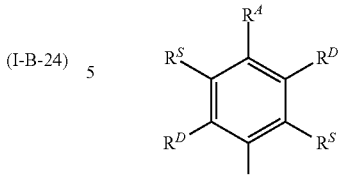 (I-B-31)

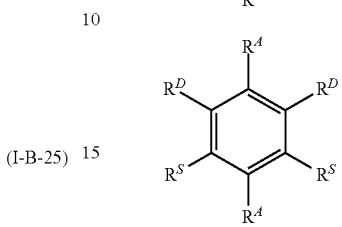 (I-B-32)

Particularly well suited examples of the compounds of formula (II) are those selected from formulae (I-B-1) to (I-B-12), (I-B-16) to (I-B-24) and (I-B-26) to (I-B-32), wherein $R^A$ is —CN and $R^D$ is carbazol or a substituted carbazol.

For the present compounds of general formula (I) $R^A$, $R^D$, $R^S$, a, b and c may be selected as defined herein, provided that for (i) a=2, b=4 and c=0; or (ii) a=b=c=2 and the two groups $R^S$ being in para-position to each other, and the two groups $R^A$ being in ortho-position to each other and the two groups $R^D$ being in ortho-position to each other, $R^A$ is not —CN and $R^D$ is not carbazol or a substituted carbazol. Expressed differently, for $R^A$ being —CN and $R^D$ being carbazol or a substituted carbazol the present compound cannot be any one of formulae (I-B-13), (I-B-14), (I-B-15) and (I-B-25).

Oligomers, Polymers, Dendrimers

The compounds of general formula (I), particularly such compounds comprising reactive groups, may be used as monomers for the production of the respective oligomers, polymers or dendrimers. The present invention therefore also provides for oligomers, polymers and dendrimers comprising the compound of general formula (I).

Exemplary reactive groups may—independently of each other if more than one such group is present—be selected from the group consisting of Cl, Br, I, boronic acid, esters of boronic acid, amines, alkenyl with terminal C—C-double bond, alkinyl with terminal C—C-triple bond, oxirane, oextane, groups capable of undergoing a cycloaddition, particularly a 1,3-dipolar cycloaddition (such as for example dienes or azides), derivatives of carbonic acids, alcohols and silanes. Such reactive groups may be comprised in the compounds of general formula (I) for example in groups $R^A$, $R^D$ and $R^S$ and/or also directly on a ring carbon atom, as for example in any one or more of groups $Q^1$, $Q^2$, $Z^1$ and $Z^2$. Depending upon the position of the reactive group(s) in the compound of formula (I), compound (I) may eventually be located in the main chain and/or in a side chain of the oligomer, polymer or dendrimer.

For the purposes of the present application an oligomer is understood to comprise at least 3 repeating units, and a polymer is understood to comprise at least 10 repeating units, such repeating units comprising at least one compound of general formula (I). It is noted that the above definitions in respect to the compound of formula (I) also apply here.

The oligomers, polymers and dendrimers of the present invention may be conjugated, partially conjugated or not conjugated. They may also be linear, branched or dendritic. In a linear structure the repeating units may either consist of a suitable compound of formula (I) or may be linked by means of a bivalent group, such as for example a substituted or unsubstituted alkylene group, a heteroatom or a bivalent aromatic or heteroaromatic group. In branched or dendritic structures three or even more suitable compounds of general formula (I) may be linked by means of a tri- or even higher-valent group, for example by means of a trivalent or higher-valent aromatic or heteroaromatic group, so as to form a branched or dendritic oligomer or polymer.

The present oligomers or polymers may be either homopolymerized or copolymerized in presence of at least one further monomer, in the following referred to as "comonomer". Suitable comonomers may be selected from the list consisting of fluorenes (for example those disclosed in EP 842208 or WO 00/22026), spirobifluorenes (for example those disclosed in EP 707020, EP 894107 or WO 06/061181), para-phenylenes (for example those disclosed in WO 1992/18552), carbazoles (for example those disclosed in WO 04/070772 or WO 2004/113468), thiophenes (for example those disclosed in EP 1028136), dihydrophenanthrenes (for example those disclosed in WO 2005/014689 or WO 2007/006383), cis- and trans-indenofluorenes (for example those disclosed in WO 2004/041901 or WO 2004/113412), ketones (for example those disclosed in WO 2005/040302), phenanthrenes (for example those disclosed in WO 2005/104264 or WO 2007/017066) and blends of any one or more of these.

The present oligomers, polymers and dendrimers may comprise further components such as for example emitting compounds, of which vinyltriarylamines (for example those disclosed in WO 2007/068325) or metal complexes (for example those disclosed in WO 2006/003000), and/or charge transporting components, particularly those comprising triarylamines.

The present oligomers, polymers and dendrimers may generally be produced by well-known polymerization methods. As particularly well suited polymerization methods leading to the formation of C—C or C—N bonds the following may be mentioned:
(A) SUZUKI-polymerization;
(B) YAMAMOTO-polymerization;
(C) STILLE-polymerization; and
(D) HARTWIG-BUCHWALD-polymerization.

These methods including the respective polymerization conditions are well known to the skilled person and are also described in detail in the literature, for example in WO 2003/048225, WO 2004/037887 and WO 2004/037887.

Hence, the present application also provides for a method to produce the above oligomers, and polymers by polymerization according to a method selected from the group consisting of Suzuki-polymerization, Yamamoto-polymerization, Stille-polymerization, and Hartwig-Buchwald-polymerization. The respective dendrimers may be produced according to these methods or similar methods. Suitable methods for producing such dendrimers are for example disclosed in Jean M. J. Frechet, Craig J. Hawker, "Hyperbranched polyphenylene and hyperbranched polyesters: new soluble, three-dimensional, reactive polymers", Reactive & Functional Polymers (1995), 26(1-3), 127-36; H. M. Janssen, E. W. Meijer, "The synthesis and characterization of dendritic molecules", Materials Science and Technology (1999), 20 (Synthesis of Polymers), 403-458; Donald A. Tomalia, "Dendrimer molecules", Scientific American (1995), 272(5), 62-6; WO 2002/067343 A1; and WO 2005/026144 A1.

The compounds and polymers according to the present invention can also be used in mixtures or polymer blends, for example together with monomeric compounds or together with other polymers having charge-transport, semiconducting, electrically conducting, photoconducting and/or light emitting semiconducting properties, or for example with polymers having hole blocking or electron blocking properties for use as interlayers or charge blocking layers in OLED devices. Thus, another aspect of the invention relates to a polymer blend comprising one or more polymers according to the present invention and one or more further polymers having one or more of the above-mentioned properties. These blends can be prepared by conventional methods that are described in prior art and known to the skilled person. Typically the polymers are mixed with each other or dissolved in suitable solvents and the solutions combined.

Formulation

Another aspect of the invention relates to a formulation comprising one or more compounds of formula (I), oligomers, polymers, dendrimers or polymer blends as described above and below and one or more organic solvents. Such formulation may be a solution, a suspension or an emulsion. The manufacture of such formulations is well known and for example disclosed in WO 2002/072714, WO 2003/019694 and the literature cited therein.

Suitable organic solvents may for example be selected from the group consisting of toluene, anisol, o-xylene, m-xylene, p-xylene, methylbenzoate, mesitylene, tetraline, 1,2-dimethoxybenzene (commonly known as "veratrole"), tetrahydrofurane (commonly abbreviated as "THF"), methyl-tetrahydrofurane, tetrahydropyrane (oxane), chlorobenzene, dioxane, phenoxytoluene, particularly 3-phenoxytoluene, (-)-fenchone, 1,2,3,5-tetramethylbenzene, 1,2,4,5-tetramethylbenzene, 1-methylnaphthaline, 2-methylbenzothiazole, 2-phenoxyethanol, 2-pyrrolidinone, 3-methylanisole, 4-methylanisole, 3,4-dimethylanisole, 3,5-dimethylanisole, acetophenone, α-terpineol, benzothiazole, butylbenzoate, cumene, cyclohexanol, cyclohexanone, cyclohexylbenzene, decalin, dodecylbenzene, ethylbenzoate, indane, N-methyl-2-pyrrolidone (commonly abbreviated as "NMP"), p-cymene, ethyl phenyl ether, 1,4-diisopropylbenzene, dibenzylether, diethylenglycolbutylmethylether, triethylenglycolbutylmethylether, diethylenglycoldibutylether, triethylenglycol-dimethylether, diethylenglycolmonobutylether, tripropylenglycoldimethylether, tetraethylenglycoldimethylether, 2-isopropylnaphthaline, pentyl-benzene, hexylbenzene, heptylbenzene, octylbenzene, 1,1-bis(3,4-dimethyl-phenyl)ethane and blends of any of these.

Organic Electronic Devices

The compound, oligomer, polymer and dendrimer of the present invention can be used as active material in an organic electronic device. The term "active material" is used herein to denote for example charge injection materials, charge transport materials, charge blocking materials, emitting materials or matrix materials.

Preferably such organic electronic device comprises an anode, a cathode and an active layer, said active layer comprising said active material. Organic electronic devices of the present invention include, without limitation, optical, electrooptical, electronic, electroluminescent and photoluminescent devices. Examples thereof include, without limitation, organic field effect transistors (OFETs), organic thin film transistors (OTFTs), organic light emitting diodes (OLEDs), organic light emitting transistors (OLETs), organic photovoltaic devices (OPVs), organic photodetectors (OPDs), organic solar cells, laser diodes, Schottky diodes, photoconductors, and photodiodes. Preferably, the present devices are selected from the group consisting of organic light emitting diodes, and organic light emitting transistors. Most preferably the present devices are organic light emitting diodes.

In addition to the anode, cathode and active layer, the present organic electronic device may optionally comprise at least one further layer selected from the group consisting of electron transport layer, hole transport layer, hole injection layer, electron injection layer, exciton blocking layer, interlayers, and charge generation layer. The presence (or absence) of such further layers depends upon the type of organic device and the respective final use.

Because the present compound, oligomer, polymer or dendrimer show particularly advantageous properties when used as light emitting material in organic electroluminescent devices, it is preferred to use these as light emitting materials in light emitting layers of such devices.

If the organic electronic device of the present invention is an organic electroluminescent device it comprises an anode, a cathode and a light emitting layer. Optionally, in addition to these it may comprise one or more further layers selected from the group consisting of hole injection layer, hole transport layer, hole blocking layer, electron injection layer, electron transport layer, electron blocking layer, charge generation layer, exciton blocking layer, organic p/n-transition layer and inorganic p/n-transition layer. It may also be possible that one or more hole transport layers comprise a p-dopant. Exemplary p-dopants are metal oxides and (per) fluorinated electron-deficient aromatics. Examples of suitable metal oxides are—without limitation—$MoO_3$ and $WO_3$. It is also possible that—independent of any doping of a hole transport layer—one or more electron transport layers are doped with a n-dopant. Optionally, interlayers may be present between two light emitting layers—if such are present, which for example have an exciton blocking function and/or direct the charge equilibrium in the organic electroluminescent device.

The present organic electronic devices may also have more than one light emitting layer. In such a case it is preferred that the different light emitting layers have different emission maxima between 380 nm and 750 nm, thereby allowing the emission of light of different colors, and resulting for example in the emission of white light. Particularly preferred in this respect are organic electronic devices comprising three light emitting layers, wherein preferably at least one of these comprises the compound, oligomer, polymer or dendrimer of the present application and the three light emitting layers emit in the blue, green, and orange or red. For a description of the basic structure of such a device it is for example referred to WO 2005/011013. It is noted that instead of several different light emitting compounds it is also possible to use one compound that emits in a broad range of wavelength and in sum emits white light.

In a preferred aspect of the present invention the compound of general formula (I) is used as emitter in or more light emitting layers.

If used as an emitter in a light emitting layer, the compound of formula (I) is preferably used in combination with one or more matrix materials. The mixture comprising compound of formula (I) and a matrix material preferably comprises between 0.1 vol % and 99 vol %, preferably between 1 vol % and 90 vol %, even more preferably between 3 and 40 vol %, and most preferably between 5 vol % and 15 vol % of the compound of formula (I), relative to the total volume of the mixture.

As matrix materials any suitable materials known to the skilled person may be used, preferably such materials wherein the triplet-level of the matrix material is higher than the triplet-level of the emitter.

Suitable matrix materials used herein may be selected from the following: ketones, phosphinoxides, sulfoxides, sulfones, triarylamines, carbazol-derivatives, indolocarbazole-derivatives, indenocarbazole-derivatives, azacarbazoles, bipolar matrix materials, silanes, azaboroles, boronic acid esters, diazasilole-derivatives, triazine-derivatives, zinc-complexes, dibenzofurane-derivatives and bridged carbazole-derivatives. Suitable examples of sulfoxides and sulfones are for example disclosed in WO 2004/013080, WO 2004/093207, WO 2006/005627 or WO 2010/006680. Suitable derivatives of carbazoles are for example CBP (N,N-Bis-carbazolylbiphenyl), m-CBP or the ones disclosed in WO 2005/039246, US 2005/0069729, JP 2004/288381, EP 1205527, WO 2008/086851 and US 2009/0134784. Suitable derivatives of indolocarbazole are for example the ones disclosed in WO 2007/063754 or WO 2008/056746. Suitable examples of derivatives of indenocarbazole are for example the ones disclosed in WO 2010/136109 or WO 2011/000455. Suitable examples of azacarbazoles are for example disclosed in EP 1617710, EP 1617711, EP 1731584, or JP 2005/347160. Suitable examples of bipolar matrix materials are for example disclosed in WO 2007/137725. Suitable examples of silanes are for example disclosed in WO 2005/111172. Suitable examples of azaboroles or boronic acid esters are for example disclosed in WO 2006/117052. Suitable derivates of diazasiloles are for example disclosed in WO 2010/054729. Suitable derivatives of diazaphospholes are for example disclosed in WO 2010/054730. Suitable derivatives of triazine are for example disclosed in WO 2010/015306, WO 2007/063754 or WO 2008/056746. Suitable zinc-complexes are for example disclosed in EP 652273 or WO 2009/062578. Suitable derivatives of dibenzofuranes are for example disclosed in WO 2009/148015. Suitable examples of bridged derivatives of carbazole are for example disclosed in US 2009/0136779, WO 2010/050778, WO 2011/042107 or WO 2011/088877.

Alternatively the compound, oligomer, polymer or dendrimer of the present application may be present in any of the other layers present in the organic electronic device, such as for example in the electron transport layer.

Preferably, the sequence of layers is as follows:
anode,
optional hole injection layer,
optional one or more hole transport layer,
light emitting layer,
optional electron transport layer,
optional electron injection layer, and
cathode.

It is noted that any layer indicated as "optional" may either be present or absent, depending upon the intended use and/or desired properties of the resulting device.

The anode is generally formed of an electrically conductive material. Exemplary electrically conductive materials include electrically conductive metals, electrically conductive alloys, electrically conductive polymers, and electrically conductive metal oxides. Exemplary electrically conductive metals include gold, silver, copper, aluminum, nickel, palladium, platinum, and titanium. Exemplary electrically conductive alloys include stainless steel (e.g., 332 stainless steel, 316 stainless steel), alloys of gold, alloys of silver, alloys of copper, alloys of aluminum, alloys of nickel, alloys of palladium, alloys of platinum, and alloys of titanium. Exemplary electrically conducting polymers include polythiophenes (e.g., doped poly(3,4-ethylenedioxythiophene)), polyanilines (e.g., doped polyanilines), polypyrroles (e.g., doped polypyrroles). Exemplary electrically conducting metal oxides include indium tin oxide, indium zinc oxide, fluorinated tin oxide, tin oxide and zinc oxide. It is preferred that the anode is formed of a material with high work function, for example with a work function of at least 4.5 eV versus vacuum. In some embodiments, blends or combinations of electrically conductive materials are used. In some embodiment, it may be advantageous to form the anode of transparent material, such as for example indium tin oxide or indium zinc oxide. Alternatively the anode may comprise more than one layer, for example it may comprise an inner layer of indium tin oxide and an outer layer of tungsten oxide, molybdenum oxide or vanadium oxide.

The cathode is generally formed of an electrically conductive material, preferably one with a low work function. Exemplary materials suitable are metals such as earth alkaline metal, main group metals or lanthanide. Particular examples of such metals are Ca, Ba, Mg, Al, In, Yb, Sm and Eu as well as alloys thereof. It is also possible to use alloys of silver and an alkaline metal or alkaline earth metal, such as for example an alloy of silver and magnesium. The cathode may also be formed of more than one layer, in which case metals or alloys having a higher work function may be present. Examples of such metals or alloys having a higher work function are Ag, Al, Ca/Ag alloy, Mg/Ag alloy and Ba/Ag alloy.

In some embodiments the cathode may also comprise a layer of material having a high dielectric constant. Examples of suitable materials are metal fluorides, oxides or carbonates with the metal selected from the alkaline and alkaline earth metals. Specific examples of such materials are LiF, $Li_2O$, $BaF_2$, MgO, NaF, CsF, $Cs_2CO_3$ or $CaF_2$. Lithium chinolate may also be used.

Further suitable materials for a charge transport layer, for example for a hole transport layer or an electron transport layer, are for example disclosed in Y. Shirota et al., Chemical Reviews 2007, 107(4), 953-1010. Suitable examples are aluminum complexes, zirconium complexes, benzimidazole, triazine, pyridine, pyrimidine, pyrazine, chinoxaline, chinoline, oxadiazole, aromatic ketones, lactame, borane, diazaphosphole, phosphinoxide and their derivatives as for example disclosed in JP 2000/053957, WO 2003/060956, WO 2004/028217, WO 2004/080975 or WO 2010/072300.

Preferred examples of hole transport materials, which may be used in a hole transport, hole injection or electron blocking layer, are derivates of indenofluorene amine (e.g. disclosed in WO 06/122630 or WO 06/100896), amines (e.g. the amines disclosed in EP 1661888 or those disclosed in WO 95/09147), derivaties of hexaazatriphenylene (e.g. disclosed in WO 01/049806), derivatives of amines with annealed aryls (e.g. as disclosed in U.S. Pat. No. 5,061,569), monobenzoindenofluorenamines (for example as disclosed in WO 08/006449), dibenzoindenofluorenamines (for example as disclosed in WO 07/140847), spirobifluoreneamines (for example as disclosed in WO 2012/034627), fluorene-amines, spiro-dibenzopyrane-amines and derivatives of acridine.

In order to avoid or reduce the damaging effects of water and air the organic electronic device of the present invention is subsequently enclosed and sealed.

The present compound, oligomers, polymers or dendrimers as defined above, or alternatively their respective formulations as defined above, may be used in the production of organic electronic devices, particularly organic light emitting diodes (OLEDs). In particular, they are useful in the production of the light emitting layer of an organic light emitting diode.

The organic electronic device of the present invention may be produced by any suitable method. For example, one or more layer comprised in such organic electronic device may be deposited by sublimation, by organic vapor phase deposition (OPVD), by carrier gas sublimation, by organic vapor jet printing, by spin-coating or by any printing method, such as for example screen-printing, ink-jet printing, flexographic printing, or light induced thermal imaging.

Hence, the present invention also provides for a method for producing the present electronic devices, said method comprising the steps of
(a) providing the compound, polymer, oligomer or dendrimer of the present invention; and
(b) depositing said compound, polymer, oligomer or dendrimer on a supporting layer.

The present organic electronic devices may for example be used in displays, light sources in lighting appliances as well as for example in medical and cosmetic appliances.

It is believed that the compounds, oligomers, polymers and dendrimers of the present invention are to have particularly advantageous properties in organic light emitting devices because of the reduced energy difference between S1-level and T1-level, which have been confirmed by calculations. Without wishing to be bound by theory it is believed that this is the result of the particular arrangement of substituents on the six-membered ring of the compound of the present invention. The calculations furthermore indicate that the compounds of the present invention will emit in the blue region and as such are particularly desirable for use in organic light emitting compounds.

The invention claimed is:
1. A compound of formula (I-B-22)

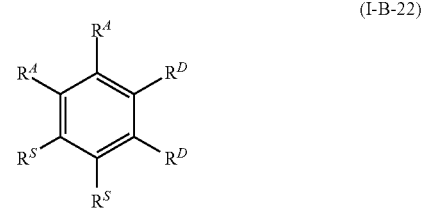

(I-B-22)

wherein
$R^A$ is at each occurrence independently a group with −M-effect and is selected from the group consisting of fluoroalkyl and aryl substituted with one or more electron withdrawing groups, wherein the electron withdrawing groups are selected from the group consisting of fluoroalkyl, F and CN;
$R^D$ is at each occurrence independently a group with +-M-effect;
$R^S$ is at each occurrence independently selected from the group consisting of linear alkyl group with 1 to 20 C-atoms or a branched or cyclic alkyl-, alkoxy- or thioalkyl-group with 3 to 20 C-atoms wherein these groups may be substituted with one or more of groups $R^2$ and wherein one or more H-atoms in these groups may be replaced by D, or an aromatic ring system with 5 to 60 aromatic ring atoms, which can be substituted with one or more groups $R^2$; and $R^2$ is at each occurrence independently selected from group consisting of H, D, aliphatic, aromatic and/or heteroaromatic hydrocarbyl group with 1 to 20 C-atoms, wherein two or more groups $R^2$ together may form a mono- or polycyclic aliphatic ring system.

2. The compound according to claim 1, wherein $R^D$ is at each occurrence independently a group of general formula (II)

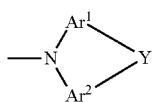

wherein $Ar^1$ and $Ar^2$ are independently of each other selected from substituted or unsubstituted aryl or heteroaryl with 5 to 30 aromatic ring atoms;

Y is selected from the group consisting of a single bond, $BR^1$, $C(R^1)_2$, $Si(R^1)_2$, $NR^1$, $PR^1$, $P(=O)R^1$, $P(=S)R^1$, O, S, S=O and $S(=O)_2$; and $R^1$ is at each occurrence independently selected from the group consisting of H, D, $B(OR^{21})_2$, CHO, $C(=O)R^{21}$, $CR^{21}=C(R^{21})$, CN, $C(=O)OR^{21}$, $C(=O)N(R^{21})_2$, $Si(R^{21})_3$, $N(R^{21})_2$, $NO_2$, $P(=O)(R^{21})_2$, $OSO_2R^{21}$, $OR^{21}$, $S(=O)R^{21}$, $S(=O)_2R^{21}$, OH, SH, linear alkyl-, alkoxy- or thioalkyl-group with 1 to 20 C-atoms or a branched or cyclic alkyl-, alkoxy- or thioalkyl-group with 3 to 20 C-atoms or an alkenyl- or alkinyl-group with 2 to 20 C-atoms, wherein these groups may be substituted with one or more of groups $R^2$ and wherein one or more $CH_2$-groups in these groups may be replaced by —$R^{21}C=CR^{21}$—, —C≡C—, $Si(R^{21})_2$, C=O, C=S, $C=NR^{21}$, —C(=O)O—, —C(=O)$NR^{21}$—, $NR^{21}$, $P(=O)(R^{21})$, —O—, —S—, SO or $SO_2$, and wherein one or more H-atoms in these groups may be replaced by D, F, Cl, Br, I, CN or $NO_2$, or an aromatic or heteroaromatic ring system with 5 to 60 aromatic ring atoms, which can be substituted with one or more groups $R^{21}$ or an aryloxy- or heteroaryloxy-group with 5 to 60 aromatic ring atoms, which can be substituted with one or more groups $R^{21}$, or an aralkyl- or heteroaralkyl-group with 5 to 60 aromatic ring atoms, which can be substituted with one or more groups $R^{21}$, wherein two or more groups $R^{21}$ may be linked with each other and form an aliphatic or aromatic or heteroaromatic ring;

$R^{21}$ is at each occurrence independently selected from group consisting of H, D, F, aliphatic, aromatic and/or heteroaromatic hydrocarbyl group with 1 to 20 C-atoms, in which one or more hydrogen atoms may be replaced by F, wherein two or more groups $R^2$ together may form a mono- or polycyclic aliphatic ring system.

3. An oligomer, polymer or dendrimer comprising one or more of the compounds of claim 1, wherein at least one bond to the oligomer, polymer or dendrimer is on any one or more of groups $R^A$, $R^D$ or $R^S$.

4. A formulation comprising a solvent and the compound of claim 1.

5. A formulation comprising a solvent and the oligomer, polymer or dendrimer of claim 3.

6. An electronic device selected from the group consisting of organic integrated circuits (OICs), organic field-effect transistors (OFETs), organic thin-film transistors (OTFTs), organic light-emitting transistors (OLETs), organischen photovoltaic cells, organic optical detectors, organic photo-receptors, organic field-quench-devices (OFQDs), organic light-emitting electrochemical cells (OLECs), organic laser diodes (O-Laser) and organic electroluminescence devices (OLEDs), wherein the electronic devices comprises the compound of claim 1.

7. An organic electroluminescent device which comprises an anode, a cathode and at least one organic layer, said organic layer comprising the compound of claim 1 as matrix material in an emitting layer in combination with one or more dopants, or that it is comprised as electron transport material in an electron transport layer, an electron injection layer or a hole blocking layer.

8. An electronic device which comprises the compound as claimed in claim 1.

9. A method of producing the electronic device of claim 8, said method comprising the steps of
    (a) providing a compound of claim 1 or the oligomer, polymer or dendrimer of claim 3; and
    (b) depositing said compound or said oligomer, polymer or dendrimer on a supporting layer.

10. The compound according to claim 1, wherein $R^A$ is at each occurrence independently a group with –M-effect selected from fluoroalkyl.

11. The compound according to claim 1, wherein $R^A$ is at each occurrence independently a group with –M-effect and is selected from the group consisting of fluoroalkyl and aryl substituted with one or more electron withdrawing groups, wherein the electron withdrawing groups are selected from the group consisting of fluoroalkyl and F.

12. The compound according to claim 1, wherein $R^S$ is at each occurrence independently selected from the group consisting of a linear alkyl group with 1 to 20 C-atoms or a branched or cyclic alkyl-, alkoxy- or thioalkyl-group with 3 to 20 C-atoms wherein these groups may be substituted with one or more of groups $R^2$ and wherein one or more H-atoms in these groups may be replaced by an aromatic ring system with 5 to 60 aromatic ring atoms, which can be substituted with one or more groups $R^2$.

* * * * *